(12) United States Patent
Engin

(10) Patent No.: US 11,020,216 B2
(45) Date of Patent: Jun. 1, 2021

(54) ADJUSTABLE ELASTIC ANTAGONIST MUSCLE REPLACEMENT MECHANISM

(71) Applicant: Murat Sinan Engin, Samsun (TR)

(72) Inventor: Murat Sinan Engin, Samsun (TR)

( * ) Notice: Subject to any disclaimer, the term of this patent is extended or adjusted under 35 U.S.C. 154(b) by 305 days.

(21) Appl. No.: 15/719,590

(22) Filed: Sep. 29, 2017

(65) Prior Publication Data

US 2018/0140415 A1     May 24, 2018

Related U.S. Application Data

(63) Continuation of application No. 14/366,001, filed on Jun. 17, 2014, now Pat. No. 9,808,335.

(51) Int. Cl.
    *A61F 2/08*           (2006.01)

(52) U.S. Cl.
     CPC ........ *A61F 2/08* (2013.01); *A61F 2002/0894* (2013.01); *A61F 2210/0057* (2013.01); *A61F 2250/0003* (2013.01)

(58) Field of Classification Search
     CPC .. A61F 2002/0894; A61F 2/0811; A61F 2/08; A61F 2250/0003; A61F 2210/0057; A61F 2/0013; A61M 39/04; A61M 39/02; A61B 17/0642
     USPC ....................................... 623/13.14; 606/151
     See application file for complete search history.

(56) References Cited

U.S. PATENT DOCUMENTS

| 5,185,932 A | * | 2/1993 | Caines ...................... A61F 2/68 30/250 |
| 6,168,634 B1 | * | 1/2001 | Schmitz ................. B25J 9/1075 623/24 |
| 2009/0048479 A1 | | 2/2009 | Goria et al. |
| 2009/0318961 A1 | * | 12/2009 | Stone .................... A61F 2/0811 606/228 |
| 2010/0030332 A1 | | 2/2010 | Schedler |
| 2011/0196195 A1 | * | 8/2011 | Raven ................... A61M 39/04 600/37 |
| 2013/0226204 A1 | * | 8/2013 | Kumar ................. A61F 2/0811 606/151 |
| 2014/0039620 A1 | * | 2/2014 | Cantournet ............... A61F 2/08 623/13.14 |

FOREIGN PATENT DOCUMENTS

| CN | 201404216 Y | 2/2010 |
| DE | 19830559 C1 | 1/2000 |

(Continued)

*Primary Examiner* — Brian E Pellegrino
(74) *Attorney, Agent, or Firm* — Bayramoglu Law Offices LLC

(57) ABSTRACT

The present invention is an anatomic system which uses the principle of applying higher elastic tonus than the rest tonus of the agonist muscles to provide the function of the antagonist muscles, and which is designed in a simplest way to provide the said purpose and which can be integrated to the body. The static mechanism of the invention is an elastic mechanism which applies a continuous stable tension in order to keep the joints open. The tension of the mechanism is calibrated by increasing or decreasing the amount of the liquid in a chamber which has flexible and elastic walls up to a certain via a port. In the dynamic mechanism of the invention, the tension applied by the elastic mechanism can be changed according to the motion the patient wants to perform.

2 Claims, 5 Drawing Sheets

(56) References Cited

FOREIGN PATENT DOCUMENTS

| | | |
|---|---|---|
| DE | 20216749 U1 | 7/2003 |
| FR | 2810877 A1 | 1/2002 |
| GB | 2244006 B | 5/1994 |
| WO | 2005020857 A1 | 3/2005 |
| WO | 2011054394 A1 | 5/2011 |

* cited by examiner

ADJUSTABLE ELASTIC ANTAGONIST MUSCLE REPLACEMENT MECHANISM

CROSS REFERENCE

This application is a continuation application of application Ser. No. 14/366,001 filed on Jun. 17, 2014 which is a national phase entry of International Application No. PCT/IB2012/057612, filed on Dec. 21, 2012 which claims priority from Turkish patent Application 2011/12752, filed on Dec. 21, 2011. The content of these related applications is incorporated herein by reference.

TECHNICAL FIELD OF THE INVENTION

Skeletal muscles provide the mobility of the joints in human body. Especially in the extremities, the movement is provided by "Agonist-antagonist muscle pairs". Within this concept, for example the flexion of the wrist is provided by musculus flexor carpi radialis pair, being agonist muscles, and musculus flexor carpi ulnaris, whereas extension of the same joint is provided by antagonist muscles musculus extensor carpi radialis and ulnaris. The stronger ones of the said muscle pairs are the agonist muscles and those are the ones which generally function against the external load. The function of the antagonist muscles is to bring the extremity to the position it will function. When the antagonist muscle functions are extensively lost (especially in irrecoverable nerve lesions), even if the agonist muscles are functional, the limb cannot function and malformation is seen in the limb. The invention relates to biocompatible elastic units and the integration systems of the said units to living organism which aim to keep the functions of the antagonist muscles, which are weaker than the agonist muscles, by applying stable or variable tension.

BACKGROUND OF THE INVENTION

The surgical methods that can be applied for replacement of lost muscle functions can also be applied in antagonist muscle function losses. Tendon and muscle transfers are among the said implementations. By this means, a musculotendinous unit in willing control of the patient substitutes for the lost function of the muscle. Besides, there are some techniques specific to antagonist muscle losses. The said techniques benefit from the antagonist tonus which is not as strong as the agonist tonus. In order to eliminate the deficiency of an agonist muscle, actuator type motors, which can provide linear movement with high power, are needed and the studies for this aim continue. However, in order to eliminate the deficiency of the antagonist muscles, the mechanism which can implement higher tension than the resting tonus of agonist muscles that is the tension which they apply when the muscles do not generate any function will be adequate. The said mechanisms keep the joints at a position where they can generate function with stable tension which they implement during rest, and a person can beat the said tension with the strength of the agonist muscles when he/she wants to generate a function. Depending on the said principle, splints and orthesis were produced which provide the function of the antagonist muscles in the affected limb with the elastic systems externally. For example, in nervus radialis symptom which results in the paralysis of hand extensors, there are splints with springs which bring the wrist and the fingers to extension. The said splints keep the hand open such that it will grab an object and when the patient grabs an object, he/she beats the strength of the springs with the tension of agonist muscles and can perform the grabbing. Similarly, there are systems with spring which pull the foot upwards from its metatarsus in order to eliminate low foot seen as a result of nervus peronealis injury, and enable the patient to pull the tip of her/his foot upwards during stepping.

Tendon and muscle transfer implementations are the operations which require sacrificing the function of another muscle and requiring high technology that can be troublesome for the patient.

Both the appearance of the splints and the orthesis which will bring the joints externally to the opening wherein they will function is unpleasant and its use is difficult and their function achievement is limited. Furthermore, the said systems function with a stable tension without showing any connection with the neuromotor activity of the patient, and they cannot provide a decrease or increase in tensions such that they will adapt muscle activity intensity at a certain moment.

In addition to the said methods used practically in humans, there are several patent documents in the technique related with the object of the invention.

FR 2810877: Joint ligament implant prosthesis having elasticity and which can be fastened to the bone from both ends. However the said invention does not have a mechanism providing adjustable tension as well as it is not designed to replace a muscle function.

US 2009048479: Urethra strip manufactured from prolene mesh, developed for incontinence. Mesh pattern is also used in the project which is introduced, the structure of the mesh is commonly used and the product does not have the adjustable elastic structure in the project which is introduced.

US 2010030332, WO 2005020857: An intraocular lens model the accommodation of which can change with the contact of ciliary muscle. By means of a reservoir which can inject liquid into the said product, it can fit to the ciliary muscle and its diopter can be adjusted to a certain level, however the field of usage and operating principle is completely different from the project which is introduced.

WO2011054394 (A1): This patent is an actuator model comprised of a plurality of cells which will respond to electric current, and providing linear movement via the electro active materials inside the cells.

1—The design does not mention the use of electrorheological fluid.

2—It does not include details of how it will be used in an organism and how it will be integrated.

3—It does not mentioned concretely how it will be controlled by the individual.

CN201404216: The invention disclosed in the patent aims to amplify the myoelectric activity in the limbs and stimulate the paralyzed muscles directly. The technology in the said invention is already used in myoelectric prosthesis (electronic hand prosthesis).

DE20216749U: The invention disclosed a contraction device for generating linear force, especially for natural body movement apparatus, comprises compartments expandable by pumping in fluid.

U.S. Pat. No. 6,168,634B: The invention disclosed a hydraulically energized magnetorheological replicant muscle tissue is provided as well as a system and method for using and controlling the same. The artificial muscle tissue is capable of causing motion, inducing force and enabling control thereof with life-like action. Numerous muscle tissue elements may be combined together to form a tissue capable of causing motion, inducing force and enabling control.

Each muscle tissue element may receive fluid from a fluid supply. Control of fluid entering and exiting the muscle tissue element through valves may be effected using a central processing unit. As a result thereof, life-like action and artificial muscle tissue may be formed that replicates actual muscle tissue.

DE19830559C1: The invention disclosed a device for purposeful mechanical support and provoking of muscle portions are described at the human Körper.$The invention are preferably characterised that a flexible, closed container from a fluid-close material is intended, which as the laminar plant to a body part trained and with one magneto and/or electricalrheologic fluid is filled, and that a mechanism is intended to the rheologic fluid for the creation of a magnetic and/or electrical field, in order the viscosity and with it the rigidity of the rheologic fluid in the container to change.

GB2244006B: The invention disclosed an artificial limb for an above knee amputee has a control device (18) in the form of a piston and cylinder assembly in which chambers (26, 28) on either side of the piston (24) contain an electrorheological fluid and are linked by a passageway (44A-44E) including an electroviscous valve. The valve has two electrodes, one being a metallic valve block (38) and the other being a metallic rod (46) housed coaxially in a portion (44C) of the above-mentioned passageway. Restriction of fluid flow is achieved by applying a voltage across the electrodes. Additional restriction is achieved by means of a electromechanical valve (48). The piston and Page 1 cylinder assembly (18) is connected between upper and lower components of the prosthesis to control flexion and extension at the knee.

SUMMARY OF THE INVENTION

An adjustable elastic antagonist muscle replacement mechanism for overcoming the deficiency of the antagonist muscles of a patient and capable of implementing higher tension than the resting tonus of agonist muscles that is the tension which they apply when the muscles do not perform a voluntary action, including:
an adjustable tension chamber, which is formed from a loose polymer mesh in its middle segment, shaped like shuttle and the outer surface of which is coated with biocompatible elastomer;
a screw hole is placed on one end of the adjustable elastic antagonist muscle replacement mechanism and is configured for attaching the adjustable tension chamber to the bones;
a tendon suture is placed on the other end of the adjustable elastic antagonist muscle replacement mechanism and is configured for attaching the adjustable tension chamber to the tendons or soft tissues;
an injection port is configured to be placed subcutaneously and is connected with the adjustable tension chamber by a connection tube, by which fluid is filled in to or discharged out of the adjustable tension chamber;
a nozzle is reinforced with a hardened elastomer clamp in the least mobile proximal part of the chamber.
Wherein the connection tube is made of a biocompatible elastomer and provides the injection port connected to the nozzle.
Wherein the adjustable tension chamber is capable of applying a continuous stable tension that is higher than the resting tonus of agonist muscles between two anatomic localization for keeping joints in natural position.
Wherein the injection port is a discoid chamber with a solid back wall and a silicone rubber front wall, which allows introduction of a needle and seals itself off as the needle is withdrawn.

An adjustable elastic antagonist muscle replacement mechanism for overcoming the deficiency of the antagonist muscles of a patient and capable of implementing higher tension than the resting tonus of agonist muscles that is the tension which they apply when the muscles do not perform a voluntary action, including:
a plurality of adjustable tension chambers, which are formed from a loose polymer mesh in their middle segment, shaped like shuttle and the outer surface of which is coated with biocompatible elastomer;
a screw hole is placed on one end of the adjustable elastic antagonist muscle replacement mechanism and is configured for attaching the adjustable tension chambers to the bones;
a tendon suture is placed on the other end of the adjustable elastic antagonist muscle replacement mechanism and is configured for attaching the adjustable tension chambers to the tendons or soft tissues;
an injection port is configured to provides liquid in a desired amount being filled in to or discharged out of the adjustable tension chambers via a connection tube, wherein the injection port is configured to be placed subcutaneously;
a nozzle is reinforced with a hardened elastomer clamp in the least mobile proximal part of the chamber.
Wherein the connection tube is made of a biocompatible elastomer and provides the injection port connected to the nozzle.
Wherein the adjustable tension chambers are capable of applying a continuous stable tension that is higher than the resting tonus of agonist muscles between two anatomic localization for keeping joints in natural position.
Wherein the injection port is a discoid chamber with a solid back wall and a silicone rubber front wall, which allows introduction of a needle and seals itself off as the needle is withdrawn.

REFERENCE SIGNS

Figure 1:
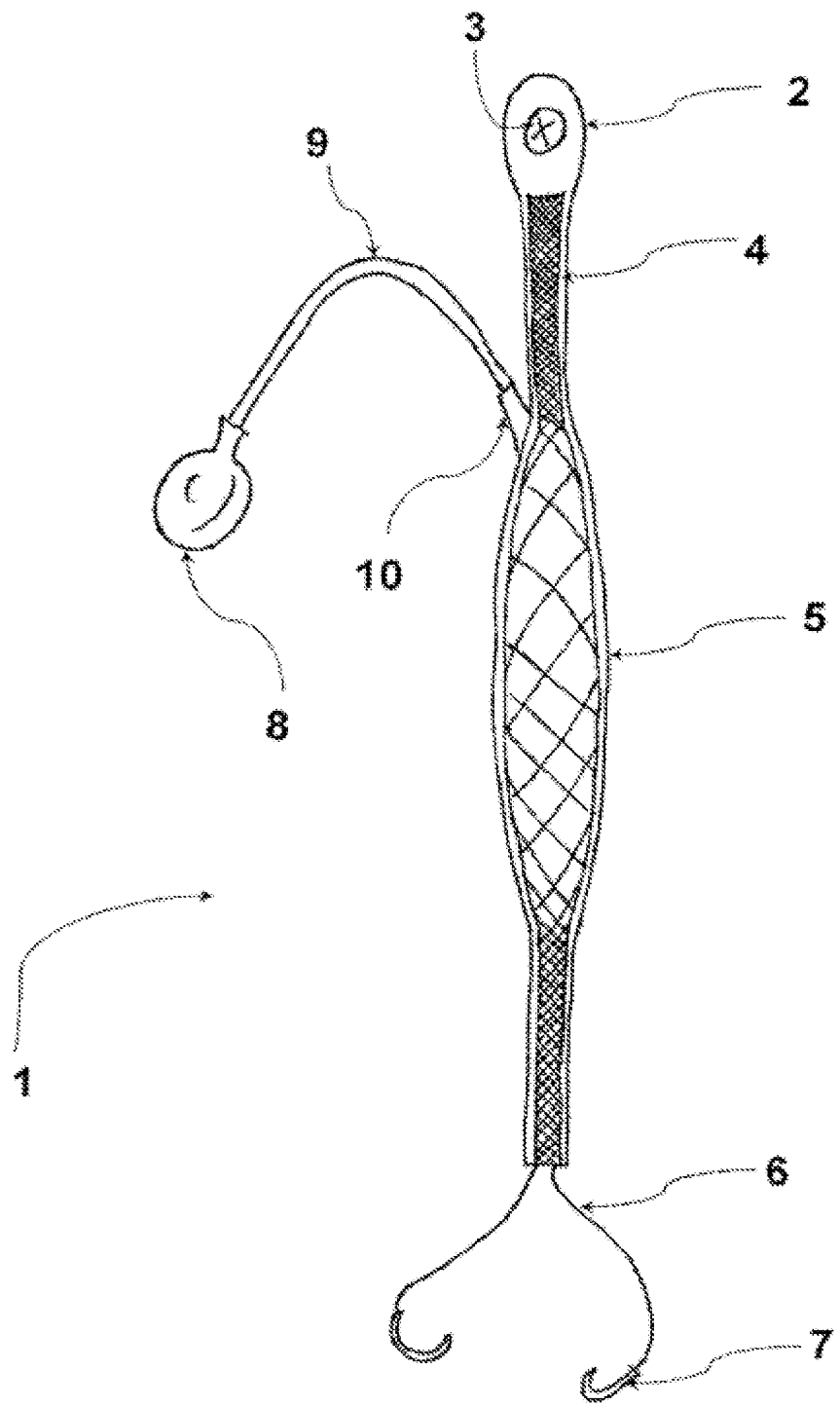
FIG. 1 is the scheme of an adjustable elastic antagonist muscle replacement mechanism (in a static structure).
Figure 2:
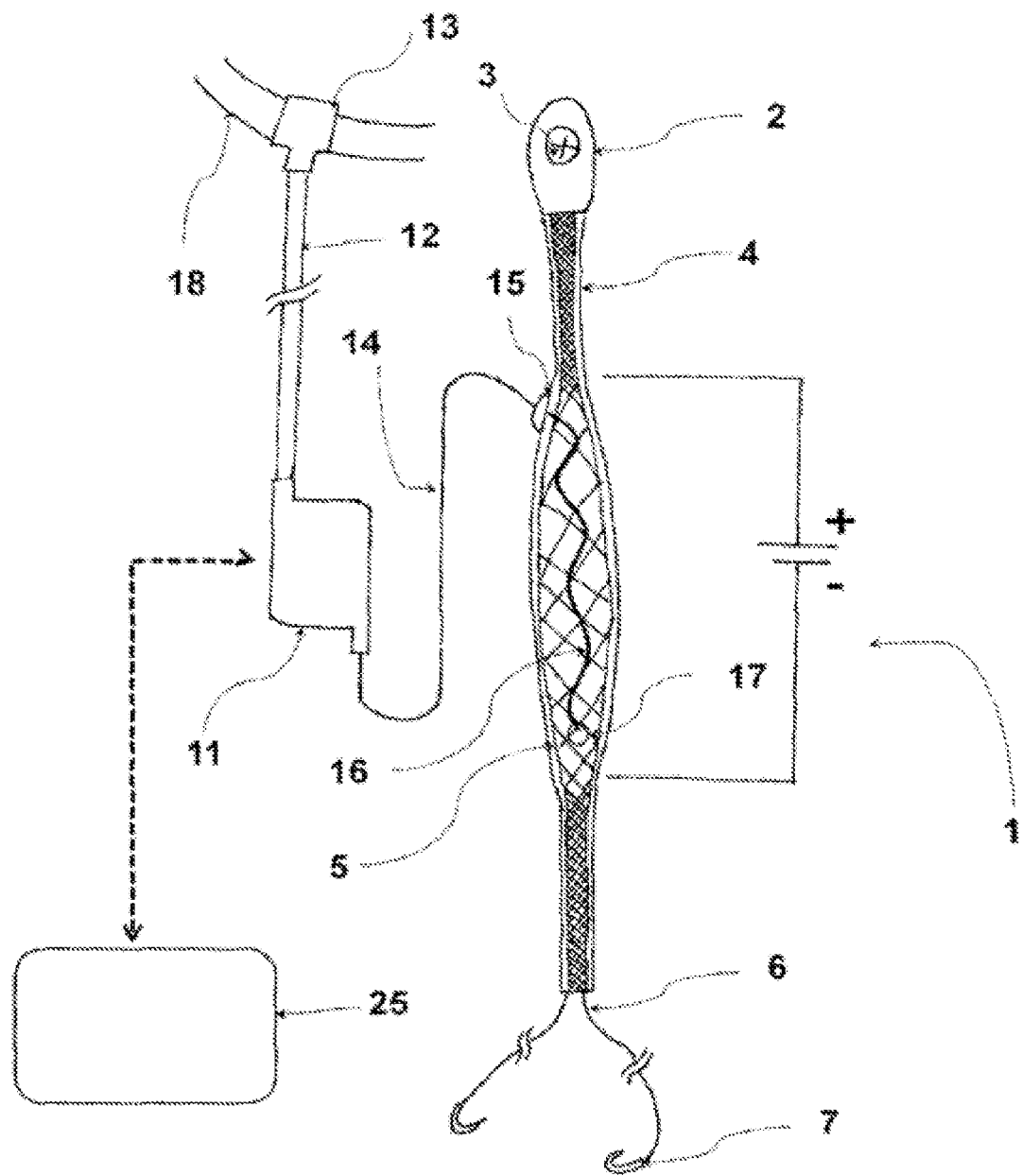
FIG. 2 is the scheme of an adjustable elastic antagonist muscle replacement mechanism (in a dynamic structure).

1. Adjustable elastic antagonist muscle replacement mechanism
2. Screw hole
3. Screw
4. Biocompatible elastomer coated close polymer mesh 5. Elastic tension chamber
6. Polymer suture
7. Suture needle
8. Injection port
9. Connection tube
10. Nozzle
11. Sensor-stimulator unit
12. Afferent cable
13. Sensor electrode
14. Efferent cable
15. Stimulator electrode
16. Stimulator electrode, anode cable
17. Stimulator electrode, anode end and inlet
18. Peripheral nerve
19. epicondvlus lateralis humeri
20. musculus extensor carpi radialis longus tendon
21. Triple dynamic tension module
22. Double dynamic tension module
23. nervus radialis
24. nervus medianus
25. External calibration unit

DETAILED DESCRIPTION OF THE INVENTION

The Static Embodiment of the Adjustable Elastic Antagonist Muscle Replacement Mechanism The static system is essentially an implant (1) produced from biocompatible materials which applies the tension to be applied by the muscle or muscle groups which have lost their function via an adjustable elastic system. The implant system is formed in a length and thickness according to the anatomic region to which it will be placed and the length and strength of the muscle which it will replace. In cases wherein a plurality of muscles which are close to each other anatomically will be replaced, the implants can be combined in a required number. The inner material of the implant is a close mesh manufactured from a biocompatible polymer (for example PEEK-CFr), its outer surface is coated with a biocompatible elastomer (for example Medical silicon) (4). The polymer mesh becomes loose in the middle part of the implant, and the silicon elastomer expands such that it will form a chamber (5) shaped like shuttle. The said part, which has a limited elasticity in its wall, is the elastic tension chamber of the mechanism and the tension strength it has can be changed with the amount of the water in its chamber (for example 0.9% isotonic NaCl). With this purpose, an injection port (8) is connected to a nozzle (10) reinforced with a hardened elastomer clamp in the proximal part of the chamber which has the least mobility via biocompatible elastomer tube (9), and liquid in a desired amount can be filled into the chamber via an injector from the said port placed subcutaneously or the liquid inside the chamber can be discharged. The function of the implant is to apply a static tension between two points. The said two points can be bone or soft tissue (tendon, ligament etc.) depending on the situation. The end of the mechanism to be attached to the bone is a screw hole (2) comprised of pressed polymer mesh between two biocompatible polymer layer and the mechanism can be screwed to the bone from this point. At the end of the mechanism to be attached to the soft tissue or tendon, the polymer mesh ends with two polymer sutures (6) which have needle (7) in desired features. According to the condition of the anatomic region which will be reconstructed, an implant can be produced such that it will attached to the bone from both ends, to the soft tissue from both ends, or to the bone from one end, to the soft tissue from the other end.

Figure 3:
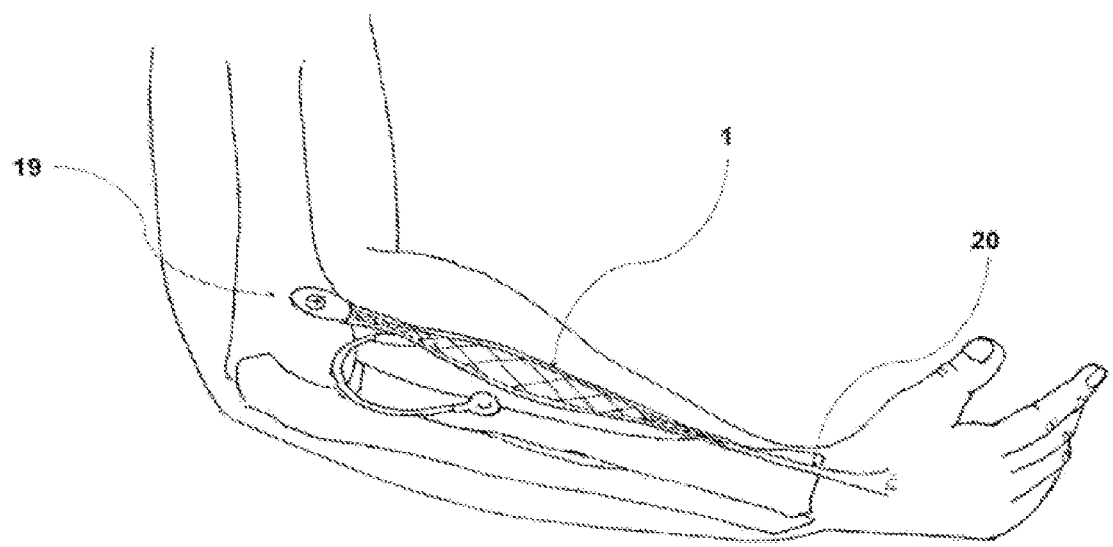
FIG. 3 is the schematic view of the embodiment of an adjustable elastic antagonist muscle replacement mechanism in a static structure.

The one shown in FIG. 1 is the version which is produced such that it will be attached to the bone from its proximal end, to the tendon from its distal end. The system (1) replacing musculus extensor carpi radialis longus muscle with demonstrative purpose is seen in FIG. 3. While the system is screwed to the epicondvlus lateralis humeri (19) from its proximal end via the screw hole, it is sutured to the extensor carpi radialis longus tendon from its distal end via the sutures (20). The system is attached such that it will keep the joints, which the muscle that will be replaced, in natural position with the chamber 30% full, and the port is left at a pouch formed under the skin. The tension provided by the system can be increased or decreased during the physiotherapy after the operation if it is necessary. After that point, the system will hold the joints of the patient open at rest. When the patient wants to produce work (like grabbing an object), he/she will perform the movement by beating the tension of the elastic system with the tonus of the agonist muscles. Similarly, the system can also be used in antagonist failures of the lower extremity.

Figure 4A:
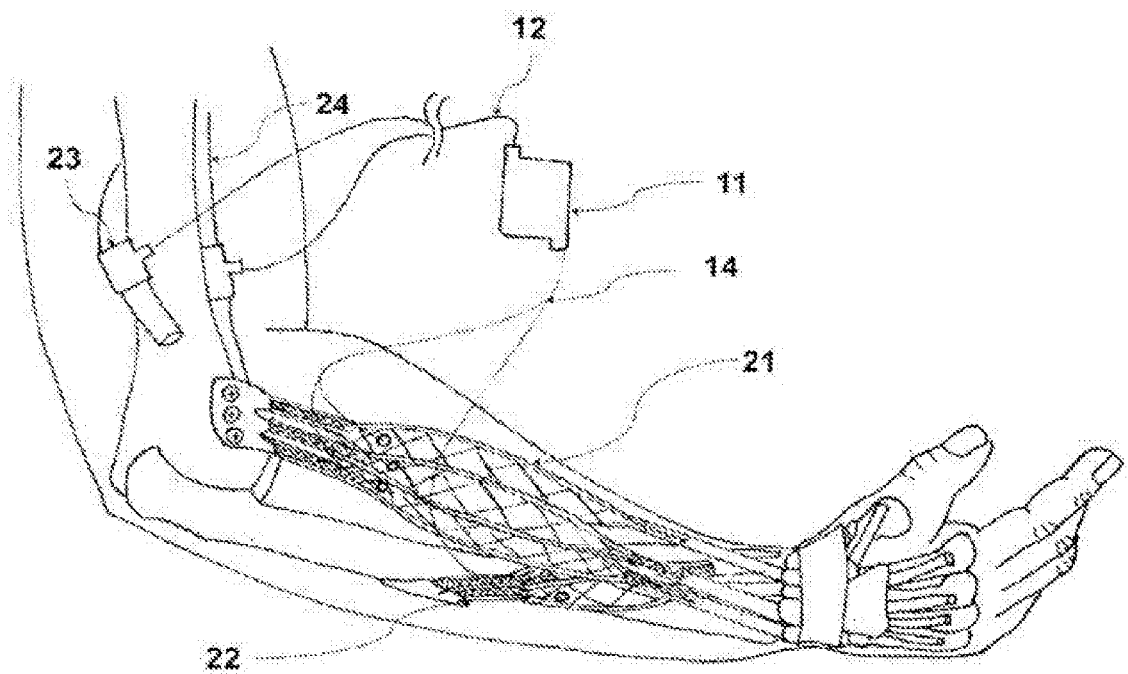
FIG. 4A is a first view of the schematic view of the embodiment of an adjustable elastic antagonist muscle replacement mechanism in a dynamic structure.
Figure 4B:
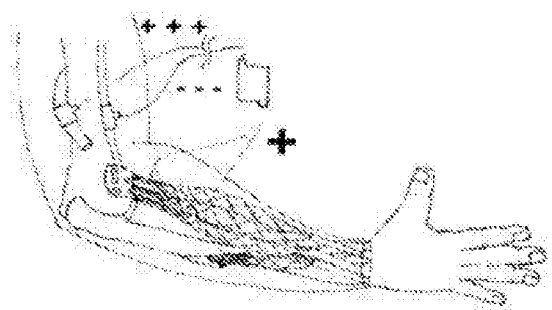
FIG. 4B is a second view of the schematic view of the embodiment of an adjustable elastic antagonist muscle replacement mechanism in a dynamic structure.
Figure 4C:
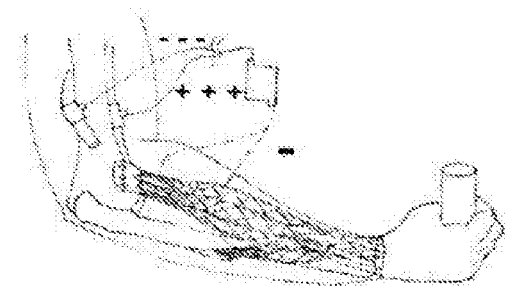
FIG. 4C is a third view of the schematic view of the embodiment of an adjustable elastic antagonist muscle replacement mechanism in a dynamic structure.
Figure 5:
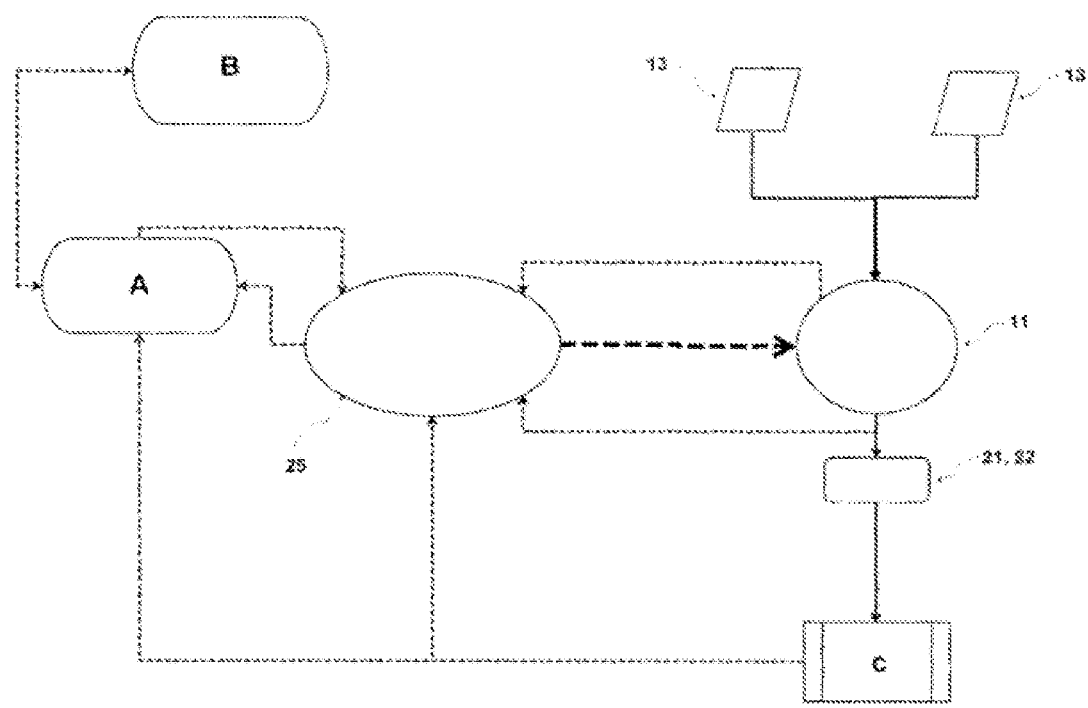
FIG. 5 is the flowchart of the sensor-stimulator system calibration and operation.

The Dynamic Embodiment of the Adjustable Elastic Antagonist Muscle Replacement Mechanism The system is essentially an implant manufactured from biocompatible materials, which applies the tension, which the muscle or muscle groups that have lost their function will apply, via an elastic system the power of which can change under the control of an electronic system which detects the muscle activity the patient wants to perform. The implant is formed in a length and thickness according to the anatomic region to which it will be placed and the length and strength of the muscle which it will replace as in the static implementation. In cases wherein a plurality of muscles which are close to each other anatomically will be replaced, the implants can be combined in a required number. The inner material of the implant is a close mesh manufactured from a biocompatible polymer (for example PEEK-CFr), its outer surface is coated with a biocompatible elastomer (for example Medical silicon) (4). Similarly, it can be attached to the compatible anatomic structures from its both ends via a screw hole (2) and screw (3) and/or tendon suture (6) and the needle (7). The difference of the dynamic system from the static system is the content of the elastic tension chamber (5). In the tension chamber similar to the one in the static system, electrorheologic fluid in a stable amount is present. The electrorheologic fluids are the liquids the viscosity of which change when they are subjected to electric current, and the electric current to be applied to the tension chamber is controlled by a sensor-stimulator unit (11) which detects the electric activity generated by the peripheral nerves (18) of the patient via sensor electrode (13) and an afferent cable system (12). The unit transfers the electric current to the stimulator electrode (15) at the proximal end of the chamber via an efferent cable (14). The cathode end of the electrode passes the wall of the elastic unit and contacts the fluid, and the insulated anode cable (16) goes until the distal end of the chamber in a curved way and reaches the content of the chamber passing through the inlet (17) supported by the elastomer disc reinforced in that region. In FIG. 4A, the embodiment of the system is shown such that it will replace all basic forearm extensors. Triple module shown as number 21 is screwed to the bone at proximal and fixed on the tendon at distal such that it will replace the extensor carpi radialis, extensor digitorum communis and extensor carpi ulnaris muscles, and the double module shown as number 22 21 is screwed to the bone at proximal and fixed on the tendon at distal such that it will replace the abductor pollicis longus ve extensor pollicis longus muscles. The sensor electrodes (13)

of the microprocessor unit can be connected to the proximal end of the antagonist radial nerve (23) which is injured or to the agonist median nerve (24) which is healthy or both according to the surgical anatomy. Stimulator electrodes (15) are connected to the related tension units. The attachment is performed in a tension such that it will keep the hand joints at a natural position when the system is in 30% tension potential, and the sensor-stimulator unit (11) is left in a pouch formed under the skin. During physiotherapy after the operation, sensor-stimulator unit is calibrated such that it will provide tension compatible with the desired movement (FIG. 5). For this, a wireless connection is formed between the sensor-stimulator unit (11) implanted to the patient (B) and the external calibration terminal (25) which is controlled by the paramedic (A) who follows the patient. As the patient makes effort to perform a certain movement willingly, the reflection of this effort on the sensor electrode(s) (13) is digitalized by the unit and sent to the external calibration terminal (25). When the data processed by the operator continuously in contact with the patient is gathered such that it will be described as a new stimulant pattern, the stimulant patterns can be matched with the motion patterns. At this point, the calibration data (thick interrupted line) are loaded to the sensor-stimulator unit, and the unit sends the stimulus which will provide the desired tension to the tension units (21, 22) when it detects the stimulant pattern. As a result, a motion (C) is generated. Under the supervision of the operator, calibration and error control feedbacks received from the patient, sensor-stimulator unit and the motion that is generator are processed and after it is confirmed that they transform into an antagonist tonus that will form the desired motion pattern of the willing effort, the calibration data takes its final form and the connection between the sensor-stimulator unit and the external calibration terminal is ended. After this point, the sensor-stimulator unit can adjust the tension of the mechanism when the sensor receives a stimulant pattern which it can identify from the electrodes independent from the external calibration terminal. In a manner of speaking, in the example of FIG. 4A, both the median and the radial nerve to which the sensor electrodes are connected reflect rest potential, and the system applies antagonist tension such that it will keep the hand in neutral position. In FIG. 4B, upon the patient wants to perform extension, inhibition potentials will be reflected on the median nerve innerving the agonist muscles, and the excitation potentials will be reflected on the stump of the radial nerve innerving the antagonist muscles. The sensor-stimulator unit calibrated appropriately will identify the said changes and increase the viscosity of the electrorheologic fluid in the chamber of the unit and thus the antagonist tension power. Similarly, when the patient—in a manner of speaking—wants to grab an object, this time the unit will decrease the viscosity of the fluid, thus the antagonist tension power as a respond to the excitation in the agonist nerve and/or the inhibition at the antagonist nerve stump (FIG. 4C). The said system can transform the electrophysiological activity in the healthy nerves into a stimulant by shifting the function of the injured nerves to the healthy nerves. From this aspect, not only in this invention, it can also be used for the signal regulation of all kind of actuator or stimulators used in denerved but healthy muscles. The system can be calibrated such that it will make each unit to apply different antagonist tonus in kinder movements. Similarly, the said system can also be used in antagonist failures of the lower extremity.

What is claimed is:

1. An adjustable elastic antagonist muscle replacement mechanism which overcomes a deficiency of antagonist muscles of a patient and is adapted to apply tension to a tendon of a muscle which has lost function;
    the adjustable elastic antagonist muscle replacement mechanism comprises:
    an adjustable tension chamber, which is formed from a polymer mesh in a middle segment of the adjustable elastic antagonist muscle replacement mechanism, and the polymer mesh is coated with a biocompatible elastomer;
    the adjustable elastic antagonist muscle replacement mechanism is adapted to be affixed to a tendon and a bone;
    the adjustable elastic antagonist muscle replacement mechanism having a first end and a second end, wherein the first end is adapted to be affixed to the bone and said first end of the adjustable elastic antagonist muscle replacement mechanism is comprised of the polymer mesh pressed between two biocompatible polymer layers and a screw hole and the screw hole is adapted to attach the adjustable tension chamber to the bone;
    said second end of the adjustable elastic antagonist muscle replacement mechanism is adapted to be affixed to the tendon and said second end of the adjustable elastic antagonist muscle replacement mechanism terminates with the polymer mesh having a tendon suture connected to the polymer mesh and the tendon suture is adapted to attach the adjustable tension chamber to the tendon;
    an injection port is configured to be placed subcutaneously and is connected with the adjustable tension chamber by a connection tube, by which fluid is filled into or discharged out of the adjustable tension chamber;
    a nozzle is reinforced with a hardened elastomer clamp and is provided in the adjustable tension chamber;
    wherein the connection tube is made of a biocompatible elastomer and provides the injection port connected to the nozzle;
    wherein the adjustable tension chamber is adapted to apply a continuous stable tension that is more than a resting tonus of agonist muscles between two anatomic localizations to keep joints in a natural position;
    wherein the injection port is a discoid chamber with a solid back wall and a silicone rubber front wall, which allows introduction of a needle and the injection port is sealed off as the needle is withdrawn.

2. An adjustable elastic antagonist muscle replacement mechanism system which overcomes a deficiency of antagonist muscles of a patient and applies tension to tendons of muscles which have lost function;
    the system comprising a plurality of adjustable elastic antagonist muscle replacement mechanisms with each comprising:
    an adjustable tension chambers, which are formed from a polymer mesh in a middle segment of each adjustable elastic antagonist muscle replacement mechanism, and the polymer mesh is coated with a biocompatible elastomer,
    each adjustable elastic antagonist muscle replacement mechanism is adapted to be affixed to the tendons and bones;
    each adjustable elastic antagonist muscle replacement mechanism having a first end and a second end, wherein the first end is adapted to be affixed to the bones and said first end of each adjustable elastic antagonist muscle replacement mechanism is comprised of the polymer mesh pressed between two biocompatible polymer layers and a screw hole and the screw hole is adapted to attach each adjustable tension chambers to the bones;

said second end of each adjustable elastic antagonist muscle replacement mechanism is adapted to be affixed to the tendons and said second end of each adjustable elastic antagonist muscle replacement mechanism terminates with the polymer mesh having a tendon suture connected to the polymer mesh and the tendon suture is adapted to attach each adjustable tension chamber to a tendon;

an injection port is connected to at least one of the adjustable tension chambers by a connection tube and fluid is filled into or discharged out of the at least one of adjustable tension chambers, wherein the injection port is configured to be placed subcutaneously;

a nozzle is reinforced with a hardened elastomer clamp and is provided in the at least one of the adjustable tension chambers;

wherein the connection tube is made of a biocompatible elastomer and provides the injection port connected to the nozzle;

wherein the adjustable tension chambers are adapted to apply a continuous stable tension that is more than a resting tonus of agonist muscles between two anatomic localizations to keep joints in a natural position;

wherein the injection port is a discoid chamber with a solid back wall and a silicone rubber front wall, which allows introduction of a needle and the injection port is sealed off as the needle is withdrawn.

\* \* \* \* \*